United States Patent
Flores-Lira

(10) Patent No.: US 6,520,018 B1
(45) Date of Patent: Feb. 18, 2003

(54) ULTRASONIC INSPECTION METHOD FOR LEAD-ACID BATTERY TERMINAL POSTS

(75) Inventor: Ricardo Flores-Lira, Monterrey (MX)

(73) Assignee: Enertec Mexico, S.r.l. de C.V., Monterrey (MX)

( * ) Notice: Subject to any disclaimer, the term of this patent is extended or adjusted under 35 U.S.C. 154(b) by 127 days.

(21) Appl. No.: 09/714,895

(22) Filed: Nov. 17, 2000

(51) Int. Cl.[7] ............................................... G01N 29/10
(52) U.S. Cl. ........................................................ 73/629
(58) Field of Search ........................ 73/627, 628, 629, 73/631

(56) References Cited

U.S. PATENT DOCUMENTS 3,926,039 A * 12/1975 Zhukov et al. ................ 73/627
4,759,221 A * 7/1988 Ortlieb et al. ................. 73/602
5,511,425 A * 4/1996 Kleinert et al. ............... 73/609
5,551,296 A * 9/1996 Taran ........................... 73/627
5,887,481 A * 3/1999 Leroy et al. ............. 204/192.13

FOREIGN PATENT DOCUMENTS

JP 08287962 A * 11/1996 .......... H01M/10/06

* cited by examiner

*Primary Examiner*—Hezron Williams
*Assistant Examiner*—Rose M. Miller
(74) *Attorney, Agent, or Firm*—Harrison & Egbert

(57) ABSTRACT

An ultrasonic testing method to evaluate the structural integrity of lead-acid batteries terminal posts including the steps of transmitting ultrasonic waves from a transducer through the body of the lead-acid battery posts, detecting the internal defects in the terminal posts by a reflected echo from the internal defect, and deciding to reject or to accept a lead-acid battery by comparing and analyzing, through hardware and software, the transmitted and reflected ultrasonic waves of the bad terminal posts against the reference of transmitted and reflected ultrasonic signal of a good terminal post. The internal defects detected by this method are pores, flaws, and cracks.

4 Claims, 2 Drawing Sheets

ULTRASONIC INSPECTION METHOD FOR LEAD-ACID BATTERY TERMINAL POSTS

BACKGROUND OF THE INVENTION

This invention relates generally to a method for detecting failed lead acid batteries, and more specifically, to a method for evaluating the structural integrity of battery terminal posts on line or off line in the manufacturing plant of said batteries.

DESCRIPTION OF RELATED ART

In the manufacture of the lead-acid batteries normally used in automobiles, groups of battery plates and separators contained in separate cells are placed in a case. The cells are joined to form intercellular connections there between. Battery posts, which will form the positive and negative terminals of the battery, extend above the upper surface of the open battery case. These battery cases are adapted to receive thereon a battery cover, which has formed therein two lead bushings to be pierced by the battery posts when the cover is fitted onto the top of the case. A liquid-tight seal is then formed between the battery case and battery cover, and the final mechanical assembly is completed by fusing the battery post elements with the battery cover bushing elements to produce the desired positive and negative battery terminal posts. Later on, acid filling, battery forming, and other operations, may be conducted in order to produce a finished battery.

Battery formation consists of the electrochemical processing of a battery plate or electrode between manufacture and first discharge, which transforms the active materials into their usable form.

Often, it is desirable to ascertain whether a battery is defective or whether it is capable of being charged, or what its charge capacity is or what its present state of charge is. Detecting failed batteries has become important in order to assure the online quality of each lead-acid battery during its manufacturing. Known means which are used at present for detecting electrical defects during intermediate stages of production are of two types: firstly, devices for measuring the voltage of the batteries at the end of the forming and charging phase enabling the rejection of the batteries whose end voltage is lower than a predetermined threshold; and secondly, rapid discharge devices requiring the rejection of batteries whose voltage is insufficient after a few seconds of discharge.

Prior to the shipping of completed automotive batteries, it is desirable to "high-rate" test those batteries shorting the positive and negative terminals of those batteries while measuring the current capacity of those batteries. The testing method disclosed by Eberle is an example. This "high-rate" testing procedure is necessary since it is possible that various connections within the battery, such as intercell connections, may be cracked or otherwise be unsatisfactory such that the battery would be prevented from delivering its full capacity, as for example, under starting conditions when used in an automobile. By "high-rate" testing these batteries, deficient welds, connections, internal shorts, incomplete formation and other deficiencies within the battery will be reflected in the battery's inability to deliver "high-rate" discharge. The problem of the "high-rate" testing methods is that they do not reliably detect broken fractured battery terminal posts. In the following paragraphs some patents related to lead-acid battery testing methods will be briefly described.

Reeves et al patented a technique for detecting failed batteries while the battery is attached to one or more electronic devices, and is receiving a float charge. The float voltage minimizes the normal voltage differences between battery cells. This technique employs a ratio comparative analysis of cell voltages of a battery provided across the terminals of the battery. The comparative analysis determines a voltage threshold that identifies whether a battery has a shorted or open cell.

Burkum et al disclosed a testing device to measures the impedance of cells that form a lead acid battery, while the battery is in a float charge condition and connected to an active electrical load. The impedance measurement is made at a frequency selected to be different from those frequencies otherwise present in the charger load circuit. A first application of the testing device monitors developing defects in one or more individual cells or intercellular connections that can prevent the battery from delivering its stored energy to the load. In a second application, the testing device is used to compare the impedance of individual cells and electrical connections to locate faulty components. However, this method tends to require a significant amount of precision circuitry and is expensive.

The battery terminal voltage and the specific gravity of each cell making up a battery are indicators, which have been used to determine battery state of charge. It is standard industry practice to take periodic specific gravity measurements and to conduct visual and other checks. However, specific gravity readings do not entirely indicate a battery ability to supply power. For example, the specific gravity of each cell in a battery may indicate a fully charged ready state, but high impedance in one intercellular connection can prevent the battery from functioning as intended.

In the method described by Win de Bank, a controllably varying charging current is supplied to the battery, and the voltage produced across the battery while that, current is supplied is measured. The dynamic voltage current characteristics are obtained, as a function of the measured voltage and supplied current. This voltage current characteristic is compared to predetermined voltage current characteristics representing batteries of the type being tested in order to determine the operating condition and/or characteristics of the battery under test.

These means are insufficient for detecting small or internal short circuits and even large short circuits, which can be detected by conventional checking methods only after long storage or service periods. Moreover, they are not suitable for detecting properly, in a battery the reverse installation and forming of cells or defects such as twisted plates, lack of electrolyte and defective separators. Dupuis et al proposed a checking method and device enabling the above mentioned defects to be detected a short time after the end of the forming and charging phase, i.e. during finishing operations. This method comprises the steps of: passing a charging current pulse through the battery, measuring an elementary transient voltage at the terminal of each storage cell; and comparing elementary transient voltages with the average transient voltage of the storage cells (total transient voltage divided by the number of the storage cells). The battery is rejected if the absolute value of the difference between the average transient voltage and one of the elementary transient voltages, becomes higher than a predetermined threshold and if the sum of the maximum absolute values of the differences constantly becomes higher than a predetermined threshold.

In view of the known lead-acid battery testing methods, there are no disclosed specific methods to evaluate the physical integrity of battery terminal posts in previous patents. It should be appreciated by those skilled in the art that an improper or defected battery terminal post is substantially detrimental to the overall performance of the electric storage battery. There is also a hazard that the electric storage battery may explode causing damage to persons and/or property. In addition, the electrical connections of the positive and negative battery posts to the positive and negative battery bushings are essential to the safety of the electrical storage battery. If a battery terminal post is not properly fused to the battery bushing, the electrical storage may leak acid and/or acid fumes from the battery bushing. For these reasons, it is very important to have a reliable testing method to evaluate the physical integrity of the battery posts.

To ensure that a reliable electrical contact is maintained, the battery terminal connector must be constructed such that it will remain securely attached to the terminal post of the battery even when subjected to road vibrations and various other adverse conditions. At the same time, the battery terminal connector must permit the battery cable to be easily disconnected and reconnected from the battery terminal posts. The posts would include the retention strength of the terminal post, the ease with which the terminal post can be attached to and detached from the battery, and the ability to be reused numerous times without a significant loss in the structural integrity of the battery terminal post.

In view of the importance of the structural integrity of the battery terminal posts and because there are no known specific testing methods for detecting battery terminal post defects, an object of the present invention is to provide a new testing technique for evaluating the physical integrity of terminal posts in lead-acid batteries.

BRIEF SUMMARY OF THE INVENTION

Some of the possible battery terminal posts non-destructive testing techniques are: high rate discharge, x-ray testing, acoustic testing, gamma ray testing and ultrasonic testing. The high rate discharge is unable to detect specifically defective posts and it does not work with unformed batteries. The x-rays require special safety equipment and do not penetrate lead. Acoustic testing is unreliable to detect terminal post defects under noisy Gamma rays require even tougher security requirements than the x-ray technique. Ultrasonic testing is broadly utilized to detect defects of structural components because is a very sensitivity technique, could detect almost any imperfection is easy to perform and relatively inexpensive. However, there is no known previous application of the ultrasonic testing technique to evaluate the structural integrity of lead-acid battery components.

The basic theory utilizes the different transmission and reflection characteristics of sonic waves at a boundary between dissimilar media. When a sound wave strikes the boundary between two different transmission media, part of the energy is reflected and part is transmitted. In ultrasonic testing the time measurements between a transmitted pulse and the receipt of a reflected echo pulse from non-uniformity in the object under test is a measure of distance. However, current ultrasonic methods for detection analysis and sizing of flaws require modifications for each different application. Another object of the present invention is to provide an ultrasonic testing method for evaluating the structural integrity of battery terminal posts.

The testing method to evaluate the structural integrity of battery terminal posts, according to the present invention, comprises the steps of transmitting ultrasonic waves from a transducer through the body of the lead-acid battery posts, detecting the internal defects in the terminal posts by comparing and analyzing the transmitted and reflected ultrasonic waves of a lead-acid battery terminal post without defects against the transmitted and reflected ultrasonic waves of a lead-acid battery terminal post with defects. The echoes being received back at the transducer are processed by hardware and software means to produce a visual display signal representing the amplitude of the echoes for a range of propagation time that can be related to the distance at which the defects are located in the battery terminal post. The internal defects detected by this method are pores, flaws, and cracks.

It is another object of the present invention to offer an ultrasonic testing method to evaluate the structural integrity of battery terminal posts on line or off line during manufacture of lead-acid batteries.

It is another object of the present invention to offer a new ultrasonic testing to evaluate the structural integrity of terminal posts before or after the lead-acid battery formation process.

DETAILED DESCRIPTION OF THE INVENTION

Figure 1:
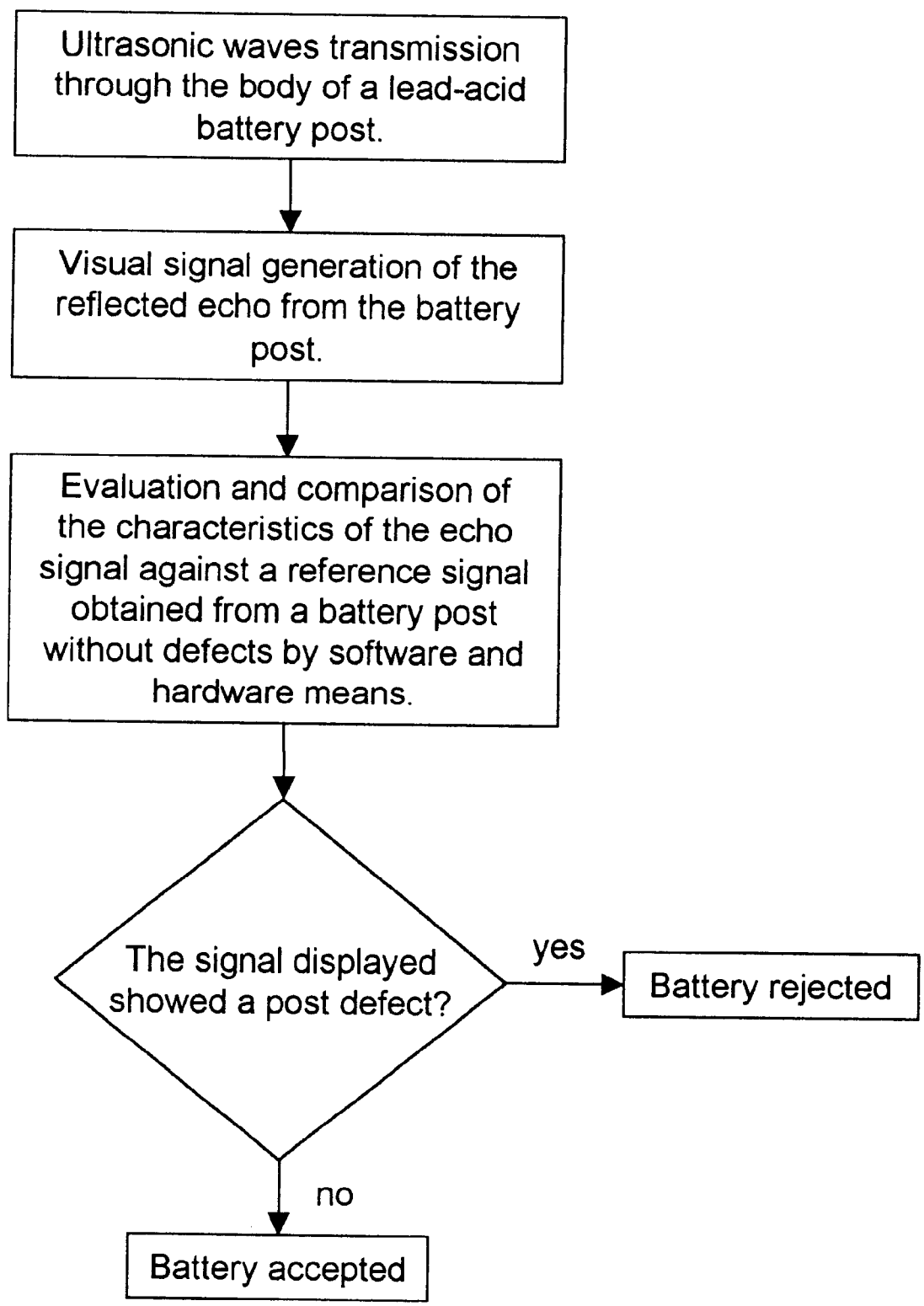
FIG. 1 is a diagrammatic illustration showing the main steps of the ultrasonic testing for detecting internal defects of lead-acid battery terminal posts in accordance with the present invention.

It should be appreciated by those skilled in the art that, flaw detector instrumentation, has been developed which not only electronically processes the returns from a flaw detection test, but also provides both digital results of the test together with a graphic display of a signal return. This allows a user to readily view amplitude versus distance display of the test result for determining whether or not a structural material under ultrasonic testing has or does not have a defect. Referring to FIG. 1, the ultrasonic testing method to detect internal defects of lead-acid battery posts, according to the present invention, comprise the following steps: transmitting ultrasonic waves from a transducer trough the body of a lead-acid battery terminal post; detecting the internal defects in the posts by a reflected echo from the internal defect in the terminal post; and deciding a condition of rejected or accepted for the lead acid-battery by comparing and analyzing, through hardware and software means, the transmitted and reflected echo of ultrasonic waves signals visually displaying internal post defects against a reference signal visually displaying a lead-acid battery post without defects. The internal defects detected by this method are pores, flaws, and cracks.

Many testing results on line and off line in manufacturing facilities, have proved that the ultrasonic testing method can be applied in massive evaluation of battery terminal posts, that it is an inexpensive testing technique (low cost per inspected unit), that it is very easy and fast to apply, that it is very reliable, and can be performed before and after the battery formation process.

Figure 2:
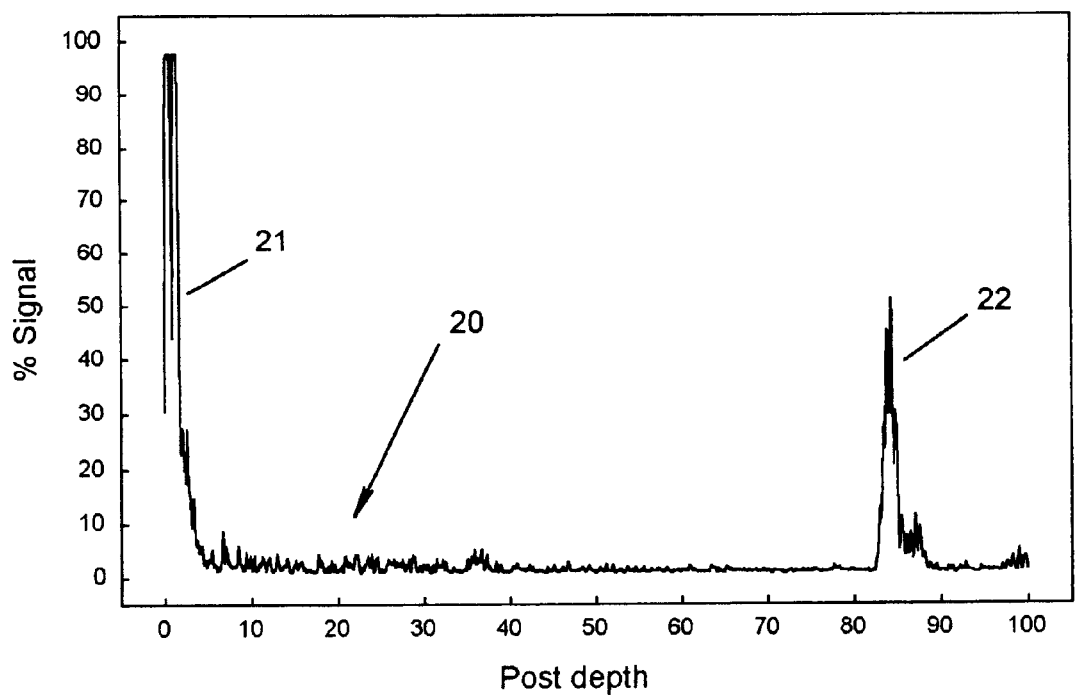
FIG. 2 is a graphic illustration of a typical ultrasonic signal for a good battery terminal post.
Figure 3:
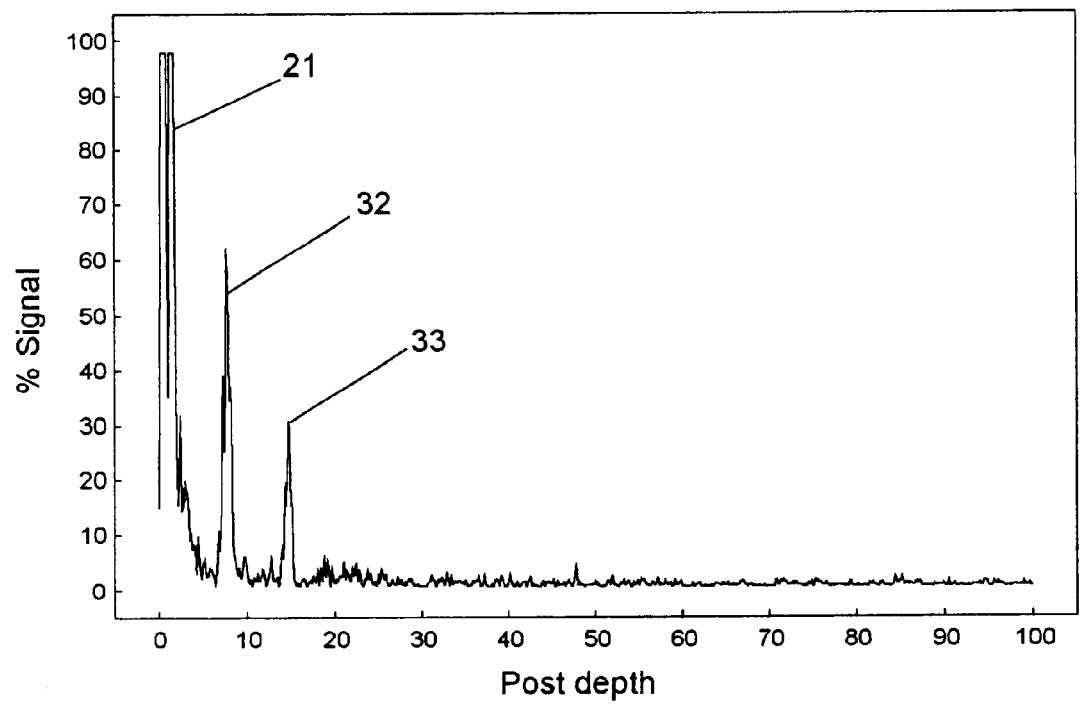
FIG. 3 is a graphic illustration of a typical ultrasonic signal for a fractured battery terminal post.

To explain in further detail the ultrasonic testing method applied according to the present invention, is shown is FIG. 2 and the FIG. 3. FIG. 2 illustrates an example in which the propagation depth of ultrasound waves signal 20, correspond to a good battery terminal post. The axis of abscissa in FIG. 2 represents the depth of a battery terminal post where the ultrasound waves are propagated, while the axis of ordinates represents the amplitude of the echo signal. The echo signal 21 and 22 of FIG. 2, represent the top and the bottom of a battery terminal post respectively. As it is shown by FIG. 2, there is not any defect-responsive echo signal between the top and the bottom of this battery terminal post. In good posts, the ultrasonic waves are able to travel all the way down through the terminal post, rebound there and return to the transducer.

FIG. 3 shows defect-responsive echo signals 12 and 13 for a cracked battery terminal post. In bad terminal posts, the ultrasonic waves rebound at the imperfections, and return to the transducer, not reaching the bottom of the terminal post. As it is known, for each distance from the transducer to the reflector, a known ultrasonic pulse will produce an echo having known characteristics. By viewing these response echo characteristics of the signal displayed for each battery terminal post and comparing them to the echo signal of a battery terminal post, the user of the method based on the present invention, can take a decision to accept or to reject a lead acid-battery. Using this method, it is also possible to detect flaws, porosity or discontinuities in battery terminal posts of lead-acid batteries.

It is another object of the present invention to offer an ultrasonic testing method to evaluate the structural integrity of battery terminal posts on line or off line during manufacture of lead-acid batteries.

It is another object of the present invention to offer a new ultrasonic testing to evaluate the structural integrity of terminal posts before or after the lead-acid battery formation process.

I claim:

1. An ultrasonic treating method for evaluating a structural integrity of a lead-acid battery terminal post comprising;

affixing an ultrasonic transducer to the terminal post;

transmitting ultrasonic waves from said ultrasonic transducer through a top of the terminal post to a bottom of the terminal post;

reflecting the ultrasonic waves off internal defects in the terminal post so as to pass as a reflected echo of the ultrasonic waves back to said ultrasonic transducer;

analyzing the reflected echo from the terminal post to determine a location of the internal defects along a length of the terminal post; and comparing the analyzed reflected echo and the transmitted ultrasonic waves against a reference signal from a terminal post without internal defects so as to make a determination as to whether to accept or reject the terminal post.

2. The method of claim 1, the internal defects being flaws.

3. The method of claim 1, the internal defects being cracks.

4. The method of claim 1, the internal defects being pores.

* * * * *